United States Patent
Key et al.

(10) Patent No.: US 10,495,553 B2
(45) Date of Patent: Dec. 3, 2019

(54) SEALING FLUID FOR MICROFLUIDIC ANALYSES

(71) Applicant: Marc Key, Ojai, CA (US)

(72) Inventors: Marc Key, Ojai, CA (US); Bipin Gupta, Pleasanton, CA (US)

(73) Assignees: Diagnostic BioSystems, Pleasanton, CA (US); Marc Key, Ojai, CA (US)

( * ) Notice: Subject to any disclaimer, the term of this patent is extended or adjusted under 35 U.S.C. 154(b) by 152 days.

(21) Appl. No.: 15/379,336

(22) Filed: Dec. 14, 2016

(65) Prior Publication Data

US 2017/0167956 A1    Jun. 15, 2017

Related U.S. Application Data

(60) Provisional application No. 62/267,402, filed on Dec. 15, 2015.

(51) Int. Cl.
*G01N 1/30* (2006.01)

(52) U.S. Cl.
CPC ......... *G01N 1/30* (2013.01); *G01N 2001/302* (2013.01)

(58) Field of Classification Search
CPC .. G01N 1/30; G01N 2001/302; Y10T 436/25; Y10T 436/10; Y10T 436/108331; Y10T 436/101666
See application file for complete search history.

(56) References Cited

U.S. PATENT DOCUMENTS

| 5,492,837 | A | 2/1996 | Naser-Kolahzadeh et al. |
| 6,280,702 | B1 * | 8/2001 | Carter ................. A61K 49/006 424/1.11 |
| 2010/0036062 | A1 * | 2/2010 | Okawa .................. A61K 8/894 525/474 |
| 2012/0322099 | A1 * | 12/2012 | Lapen ..................... G01N 1/30 435/40.5 |
| 2015/0087001 | A1 * | 3/2015 | Gradinaru ............... G01N 1/30 435/7.23 |

OTHER PUBLICATIONS

Müller, Immunolabelling of embryos, 2008, Methods Mol Biol., 420, 207-218. (Year: 2008).*
Zander, R.H., Four Water-Soluble Mounting Media for Microslides, Phytoneuron, 2014-32:1-4. Published Mar. 4, 2014. ISSN 2153 733X.
Keirnan, J.A., Microscopy Today, 97-10, pp. 16-17 (1997).
Ravikumar, S., et al., Mounting Media: An Overview, Journal of DR. NTR University of Health Sciences 2014: 3(Supplement-1): S1-8.

* cited by examiner

*Primary Examiner* — Lore R Jarrett
(74) *Attorney, Agent, or Firm* — Patentfile, LLC; Bradley C. Fach; Steven R. Kick

(57) ABSTRACT

The present disclosure relates to an aqueous sealing fluid for sealing a stained biological specimen present on a microscope slide for microscopic analysis. The sealing fluid protects the biological specimen from drying artifacts, protects stains performed on biological specimen from fading, and protects stains performed on biological specimens from being dissolved by organic mounting media. Methods of using the aqueous sealing fluid are also disclosed.

8 Claims, No Drawings

SEALING FLUID FOR MICROFLUIDIC ANALYSES

CROSS REFERENCE TO RELATED APPLICATION

This application claims the benefit of U.S. Provisional Application No. 62/267,402, filed Dec. 15, 2015, entitled SEALING FLUID FOR MICROSCOPE SLIDES, which is herein incorporated by reference in its entirety for all purposes.

INTRODUCTION

A biological specimen on a microscope slide may be stained by various methods to reveal, by microscopic analysis, molecular and histologic structures within the specimen. This disclosure relates to the use of a sealing fluid for sealing a stained biological specimen onto a microscope slide in preparation for microscopic analysis. The sealing fluid disclosed herein eliminates dehydration of the stained biological specimen prior to mounting, protects the stained biological specimen from drying artifacts, protects a stain(s) performed on the biological specimen from fading, and protects a stain(s) performed on the biological specimen from being dissolved by organic solvents present in a mounting media.

BACKGROUND OF THE DISCLOSURE

A biological specimen (sample) chosen for microscopic analysis, can be, for example, a tissue suspected of having a particular disease. An example of a biological sample is a tissue biopsy of a suspected cancer lesion. The biopsy may then be studied to see if it contains a particular molecular marker, or target of interest. If the target of interest is present in the biopsy then the diagnosis of cancer is confirmed, whereas if the target of interest is not present in the biopsy then the diagnosis of cancer may be ruled out.

A conventional method of preparing a biological specimen for microscopic analysis can comprise the following steps. A tissue sample is obtained and placed into a fixative for a period of time sufficient to fix it, rendering it rigid. The fixed tissue sample is dehydrated to remove all water and then embedded into a suitable embedding medium, such as paraffin. Thin sections of the tissue sample are cut from the paraffin block. Each tissue sample section is cut sufficiently thin (for example, about 4-6 u) so that it can be examined by a microscope. The thin sections are laid onto a microscope slide where they adhere to the slide via charged interactions. The paraffin in the tissue sample is then removed through the use of paraffin solvents, such as xylene, leaving the tissue behind. The tissue sample is then rehydrated by passing through a series of graded alcohols and water. Once the tissue sample (specimen) is rehydrated, it is ready for staining. Typically staining is achieved by exposing the tissue sample to one or more series of reagents (dyes/stains/chromogens). The end result of the staining is that colored areas of the tissue sample are produced. These colored areas provide a trained microscopist, such as a pathologist, with information that can be used to render a diagnosis. Frequently these stains are accurate enough to selectively stain specific molecular targets within the tissue sample, or within individual cells. Stains with this level of specificity include immunohistochemistry, immunocytochemistry, and in situ hybridization. Prior to mounting the stained biological sample on the slide, the water contained in the stained biological sample must be removed by a process called dehydration. After dehydration, a mounting medium is placed on the stained biological specimen. The mounting medium typically contains an organic solvent. Mounting the stained biological specimen improves its optical resolution and renders it acceptable for microscopic analysis. Lastly, a glass coverslip is placed onto mounting medium.

Several problems currently exist regarding the conventional methods of preparing a biological specimen (sample) for microscopic analysis.

The first problem exists in the dehydration step that occurs just before mounting the slide. The dehydrating fluid typically used is an alcohol, such as ethanol, which is soluble in water and can penetrate into the stained biological specimen and replace the water within the specimen with alcohol. Then the alcohol is replaced with an alcohol-miscible organic solvent, such as xylene, which can then penetrate into the tissue of the specimen. The alcohol-miscible organic solvent prepares the specimen for accepting a mounting medium that also contains an organic solvent. These steps are necessary because a stained biological specimen, which contains water, cannot be directly mounted into an organic mounting media (resinous mounting media) without first removing the water from the specimen. Because of the toxicity and health concerns associated with the use of alcohols and other organic solvents it is preferable to use other methods of dehydration, such as air-drying. However, air-drying frequently produces suboptimal drying artifacts, such as nuclear distortion and shrinkage.

Second, biological specimens (samples) that have been stained in preparation for microscopic analysis may be saved for re-evaluation over a period of months or years. Frequently during this extended period of storage the stains exhibit fading. Fading can be caused by prolonged exposure of the stains to the overlaying mounting medium and/or exposure to light.

Third, only stains that are resistant to organic solvents (e.g. alcohol-miscible organic solvents) used during the dehydration step, and organic solvents used during the mounting step can be utilized due to the dissolving action of organic solvents on stains. This greatly limits both the number of stains and mounting media that can be used.

What is needed is a sealing fluid that does not require dehydration or drying of a stained biological specimen prior to mounting. What is also needed is the use of a sealing fluid that decreases the use of alcohols or organic solvents, thus reducing the risk of exposure to the user. Lastly, what is needed is a sealing fluid that can be used with any stain and any mounting media.

Disclosed herein are novel sealing fluids (compositions) for sealing a biological specimen on a slide for microscopic analysis. The disclosed sealing fluids allow a biological specimen to be dehydrated without the use of organic solvents, protects the biological specimen from drying artifacts during a drying process, and can be used with any stain or any mounting media due to a protective barrier formed by the sealing fluid between the mounting medium and the stained biological specimen. The disclosed sealing fluids protect stains performed on biological specimens from becoming dissolved by organic solvents present in the mounting media, and protects stains performed on biological specimens from fading over time.

SUMMARY OF THE DISCLOSURE

Disclosed herein are aqueous sealing fluids for sealing a stained specimen, comprising: a water-soluble dehydration protectant at about 1% (w/v) to about 40% (w/v), wherein the aqueous sealing fluid is chemically inert with a stain used to stain the specimen. In some embodiments, the stained specimen comprises about 25% (w/v) or more water; or the stain used to stain the specimen is an immunohistochemistry stain, an in-situ hybridization stain, or any stain used in histology; or the stain used to stain the specimen is soluble in an organic solvent; or the stain used to stain the specimen is insoluble in an organic solvent; or the stain used to stain the specimen is: 3-Amino-9-ethylcarbazole (AEC); Fast Red TR; New Fuchsin; 3,3',5,5' Tetramethylbenzidine (TMB); horseradish peroxidase (HRP)-blue; 3,3'-diaminobenzidine; Benzidine; Variamine Blue; Fast Blue BB; Basic Fuchsin; Pararosanaline; an indoxyl phosphate; 6-Chloro-3-indoxyl phosphate; 5-Bromo-4-chloro-3-indoxyl phosphate; 3-indoxyl phosphate; a tetrazolium, Nitro blue tetrazolium; Tetranitro blue tetrazolium; Iodonitro tetrazolium; or the stain is a chromogen used in combination with a substrate and an enzyme, wherein the enzyme is a peroxidase, horseradish peroxidase, a phosphatase, or alkaline phosphatase. In another embodiment, the water-soluble dehydration protectant is: a water-soluble polymer at a molecular weight of about 5,000 to about 3,000,000; or a polyvinyl alcohol at a molecular weight of about 14,000 to about 210,000, or about 100,000 to about 500,000, or about 40,000 to about 60,000, or about 31,000; a polyvinyl acetate at a molecular weight of about 100,000 to about 500,000; or a polyvinylpyrrolidone at a molecular weight of about 10,000 to about 360,000, or about 6,000 to about 3,000,000; or a polyvinyl alcohol, a polyvinyl acetate, a polyvinylpyrrolidone, Mowiol 4-88, Mowiol 4-98, or Mowiol 40-88. In another embodiment, the aqueous sealing fluid further comprises a tissue-penetrating agent at about 1% (w/v) to about 40% (w/v). In other embodiments, the tissue-penetrating agent: is an alcohol, methanol, propanol, isopropanol, ethanol, ethyl alcohol, ethanol, glycerol, a glycerol polymer, polyethylene glycol, butanol, pentanol, propylene glycol, or ethylene glycol; or is a monohydric alcohol, a dihydric alcohol, or a polyhydric alcohol; or a monohydric alcohol with a molecular weight of less than about 32 molecular weight. In another embodiment, the aqueous sealing fluid further comprises a water-soluble ultraviolet stabilizer at about 0.05% (w/v) to about 15% (w/v). In alternative embodiments, the water-soluble ultraviolet stabilizer is: an ultraviolent absorber, an ultraviolent quencher, or a Hindered Amine Light Stabilizer (HALS), or a combination of any one or more of the above; or 2-phenylbenzimidazole-5-sulfuric acid, a benzophenone, a benzotriazole, a benzoate, carbon black, rutile titanium oxide, a nickel quencher, a compound with a 2,2,6,6-tramethylpiperidine ring, a 2-hydroxybenzophenone, a 2-hydroxybenzotriazole, a substituted acrylonitrile, or a salicylate. In other embodiments, the aqueous sealing fluid, has a viscosity of less than about 5,000 centipoise at 20 degrees Celsius; or the aqueous sealing fluid has a refractive index (RI) of about 1.4 to about 1.5, of about 1.5 to about 1.6, or about 1.52; or below about 1.7. Also disclosed herein is a stained specimen sealed with any of the aqueous sealing fluids.

Also disclosed herein are methods of sealing a stained specimen, comprising: contacting the stained specimen with an aqueous sealing fluid, wherein the aqueous sealing fluid comprises: a water-soluble dehydration protectant at about 1% (w/v) to about 40% (w/v), wherein the aqueous sealing fluid is chemically inert with a stain used to stain the specimen. In other embodiments, the stained specimen comprises about 25% (w/v) or more water; or the stain used to stain the specimen is an immunohistochemistry stain, an in-situ hybridization stain, or any stain used in histology; or the stain used to stain the specimen is soluble in an organic solvent; or the stain used to stain the specimen is insoluble in an organic solvent; or the stain used to stain the specimen is: 3-Amino-9-ethylcarbazole (AEC); Fast Red TR; New Fuchsin; 3,3',5,5' Tetramethylbenzidine (TMB); horseradish peroxidase (HRP)-blue; 3,3'-diaminobenzidine; Benzidine; Variamine Blue; Fast Blue BB; Basic Fuchsin; Pararosanaline; an indoxyl phosphate; 6-Chloro-3-indoxyl phosphate; 5-Bromo-4-chloro-3-indoxyl phosphate; 3-indoxyl phosphate; a tetrazolium, Nitro blue tetrazolium; Tetranitro blue tetrazolium; Iodonitro tetrazolium; or the stain is a chromogen used in combination with a substrate and an enzyme, wherein the enzyme is a peroxidase, horseradish peroxidase, a phosphatase, or alkaline phosphatase. In other embodiments, the water-soluble dehydration protectant is: a water-soluble polymer at a molecular weight of about 5,000 to about 3,000,000; or a polyvinyl alcohol at a molecular weight of about 14,000 to about 210,000, or about 100,000 to about 500,000, or about 40,000 to about 60,000, or about 31,000; a polyvinyl acetate at a molecular weight of about 100,000 to about 500,000; or a polyvinylpyrrolidone at a molecular weight of about 10,000 to about 360,000, or about 6,000 to about 3,000,000; or a polyvinyl alcohol, a polyvinyl acetate, a polyvinylpyrrolidone, Mowiol 4-88, Mowiol 4-98, or Mowiol 40-88. In another embodiment, the aqueous sealing fluid further comprises a tissue-penetrating agent at about 1% (w/v) to about 40% (w/v). In alternative embodiments, the tissue-penetrating agent: is an alcohol, methanol, propanol, isopropanol, ethanol, ethyl alcohol, ethanol, glycerol, a glycerol polymer, polyethylene glycol, butanol, pentanol, propylene glycol, or ethylene glycol; or is a monohydric alcohol, a dihydric alcohol, or a polyhydric alcohol; or a monohydric alcohol with a molecular weight of less than about 32 molecular weight. In one embodiment, the aqueous sealing fluid further comprises a water-soluble ultraviolet stabilizer at about 0.05% (w/v) to about 15% (w/v). In other embodiments, the water-soluble ultraviolet stabilizer is: an ultraviolent absorber, an ultraviolent quencher, or a Hindered Amine Light Stabilizer (HALS), or a combination of any one or more of the above; or 2-phenylbenzimidazole-5-sulfuric acid, a benzophenone, a benzotriazole, a benzoate, carbon black, rutile titanium oxide, a nickel quencher, a compound with a 2,2,6,6-tramethylpiperidine ring, a 2-hydroxybenzophenone, a 2-hydroxybenzotriazole, a substituted acrylonitrile, or a salicylate. In other embodiments, the aqueous sealing fluid, has a viscosity of less than about 5,000 centipoise at 20 degrees Celsius; or the aqueous sealing fluid has a refractive index (RI) of about 1.4 to about 1.5, of about 1.5 to about 1.6, or about 1.52; or below about 1.7.

Also disclosed are methods of treating a specimen, comprising: obtaining a specimen, staining the specimen with a stain, rinsing the stained specimen with an aqueous solution to obtain a hydrated stained specimen, contacting the hydrated stained specimen with an aqueous sealing fluid comprising a water-soluble dehydration protectant at about 1% (w/v) to about 40% (w/v) wherein the aqueous sealing fluid is chemically inert with a stain used to stain the specimen, allowing the sealing fluid to penetrate the hydrated stained specimen, and contacting the sealed and hydrated stained specimen with a resinous mounting media or an aqueous mounting media. In other embodiments, the stained specimen comprises about 25% (w/v) or more water; or the stain used to stain the specimen is an immunohistochemistry stain, an in-situ hybridization stain, or any stain used in histology; or the stain used to stain the specimen is soluble in an organic solvent; or the stain used to stain the specimen is insoluble in an organic solvent; or the stain used to stain the specimen is: 3-Amino-9-ethylcarbazole (AEC); Fast Red TR; New Fuchsin; 3,3',5,5' Tetramethylbenzidine (TMB); horseradish peroxidase (HRP)-blue; 3,3'-diaminobenzidine; Benzidine; Variamine Blue; Fast Blue BB; Basic Fuchsin; Pararosanaline; an indoxyl phosphate; 6-Chloro-3-indoxyl phosphate; 5-Bromo-4-chloro-3-indoxyl phosphate; 3-indoxyl phosphate; a tetrazolium, Nitro blue tetrazolium; Tetranitro blue tetrazolium; Iodonitro tetrazolium; or the stain is a chromogen used in combination with a substrate and an enzyme, wherein the enzyme is a peroxidase, horseradish peroxidase, a phosphatase, or alkaline phosphatase. In other embodiments the water-soluble dehydration protectant is: a water-soluble polymer at a molecular weight of about 5,000 to about 3,000,000; or a polyvinyl alcohol at a molecular weight of about 14,000 to about 210,000, or about 100,000 to about 500,000, or about 40,000 to about 60,000, or about 31,000; a polyvinyl acetate at a molecular weight of about 100,000 to about 500,000; or a polyvinylpyrrolidone at a molecular weight of about 10,000 to about 360,000, or about 6,000 to about 3,000,000; or a polyvinyl alcohol, a polyvinyl acetate, a polyvinylpyrrolidone, Mowiol 4-88, Mowiol 4-98, or Mowiol 40-88. Also disclosed is a method of treating a specimen, comprising: obtaining a specimen, staining the specimen with a stain, rinsing the stained specimen with an aqueous solution to obtain a hydrated stained specimen, contacting the hydrated stained specimen with an aqueous sealing fluid comprising a water-soluble dehydration protectant at about 1% (w/v) to about 40% (w/v) wherein the aqueous sealing fluid is chemically inert with a stain used to stain the specimen, allowing the sealing fluid to penetrate the hydrated stained specimen, optionally removing excess sealing fluid from the hydrated stained specimen, and contacting the sealed and hydrated stained specimen with a resinous mounting media or an aqueous mounting media. Also disclosed is a method of treating a specimen, comprising: obtaining a specimen, staining the specimen with a stain, rinsing the stained specimen with an aqueous solution to obtain a hydrated stained specimen, contacting the hydrated stained specimen with an aqueous sealing fluid comprising a water-soluble dehydration protectant at about 1% (w/v) to about 40% (w/v) wherein the aqueous sealing fluid is chemically inert with a stain used to stain the specimen, allowing the sealing fluid to penetrate the hydrated stained specimen, allowing the sealing fluid to dry, and contacting the sealed and hydrated stained specimen with a resinous mounting media or an aqueous mounting media. In other embodiments, the sealing fluid is dried for about 15 to about 30 minutes, or about 5 to about 15 minutes.

DETAILED DESCRIPTION OF THE DISCLOSURE

The following detailed description is provided to aid those skilled in the art in practicing the present disclosure. Even so, this detailed description should not be construed to unduly limit the present invention as modifications and variations in the embodiments discussed herein can be made by those of ordinary skill in the art without departing from the spirit or scope of the present inventive discovery.

As used in this disclosure and the appended claims, the singular forms "a", "an" and "the" include a plural reference unless the context clearly dictates otherwise. As used in this disclosure and the appended claims, the term "or" can be singular or inclusive. For example, A or B, can be A and B.

Ranges

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

About

The term "about" generally refers to plus or minus 10% of the indicated number. For example, "about 10%" may indicate a range of 9% to 11%, and "about 1" may mean from 0.9-1.1.

Conventional Methods

A conventional method of preparing a stained biological specimen for microscopic analysis is described below. In preparation for microscopic analysis, the stained biological specimen, contained on a microscope slide, is mounted with a mounting medium and then covered with a glass coverslip in order to improve optical resolution of the specimen.

In a typical process for mounting and examining a stained biological specimen on a microscope slide, prior to the mounting step, the slide is immersed in a series of water-miscible solvents to remove the water within the stained biological specimen. Commonly used solvents are ethanol or another alcohol. The series of water-miscible solvents typically begins with a mixture of water and a first solvent (e.g. ethanol), and gradually the solvent concentration is increased until the slide is immersed in pure first solvent (ethanol). At this point the slide and stained biological specimen are completely free of water. In the second part of a typical process the slide is then subjected to a second organic solvent (e.g. xylene) that is miscible with the first solvent (ethanol) and also miscible with the organic solvent of the mounting media. Typically, the slide would first be immersed in a mixture of the first solvent (ethanol) and second solvent (xylene). Gradually the proportion of the second solvent (xylene) would be increased until the slide was immersed in pure second solvent (xylene). At this point the slide would be ready to be overlaid with a suitable mounting medium that also contained a solvent miscible with the second solvent (xylene). After the mounting medium is overlaid it would then have a glass coverslip applied to complete the process of mounting.

Advantages of Disclosed Sealing Fluids

The disclosed sealing fluids have several advantages as compared to the media and solvents used in conventional methods. First, the sealing fluids comprise a water-soluble dehydration protectant that can directly infiltrate the stained biological specimen without the necessity of first removing water from the specimen. The sealing fluids disclosed herein eliminate the requirement for dehydration of the stained specimen using organic solvents, as is required by conventional methods. In addition, the sealing fluids can also comprise an optional tissue-penetrating agent, such as 10% (w/v) of alcohol that facilitates penetration of the water-soluble dehydration protectant into the stained biological specimen. In addition, the sealing fluid can also optionally contain one or more water-soluble UV stabilizers allowing stained specimens to be preserved longer without fading. UV radiation is known to have harmful effects on stains that cause them to fade over time.

Once the sealing fluid has penetrated into the stained tissue of the biological specimen, a number of beneficial effects are observed. First, the stained biological specimen may then be dried (e.g. by air, oven, or incubator) to facilitate water removal from the specimen while simultaneously preventing drying artifacts, such as nuclear distortion and shrinking. Second, the sealing fluid, once dried, produces a protective barrier between the stained specimen and the subsequently applied mounting medium. The protective barrier also has the effect of preventing fading of stains upon long-term storage of the slides. Although the exact nature of this protective mechanism is unknown, it is presumed to cause this effect by creating a physical barrier between the stains and the mounting medium or one of its components. Such a barrier may protect the stain from harmful chemical interactions. Finally, the sealing fluid, when dried, creates a barrier that prevents the stains from coming into contact with solvents present in mounting media. Solvents present in mounting media dissolve many of the stains currently in use. Previously, only stains could be used that were solvent resistant. However, the present invention allows any stain to be employed, even those that are not typically solvent resistant. Because the stains no longer come into contact with subsequent solvents, the strict adherence to solvent-resistant stains is no longer required. Also, since a protective barrier is formed, any mounting media can be used in combination with the disclosed sealing fluids.

In addition to providing sealing fluids that have several advantages compared to the media and solvents used in conventional methods, the disclosure also provides methods of mounting stained biological specimens on a microscope slide that have advantages over conventional mounting methods. For example, the disclosed methods eliminate the use harmful and toxic organic solvent solutions that are a health concern for laboratory workers.

Sealing Fluid

A sealing fluid is an aqueous composition (of or containing water, typically as a solvent or medium) that comprises a water-soluble dehydration protectant, and optionally a tissue-penetrating agent and/or water-soluble UV stabilizer.

The sealing fluid can comprise a water-soluble dehydration protectant at about 1% (w/v) to about 40% (w/v). For example, the sealing fluid comprises a water-soluble dehydration protectant at about 1% (w/v) to 2% (w/v), 2% (w/v) to 3% (w/v), 3% (w/v) to 4% (w/v), 4% (w/v) to 5% (w/v), 5% (w/v) to 6% (w/v), 6% (w/v) to 7% (w/v), 7% (w/v) to 8% (w/v), 8% (w/v) to 9% (w/v), 9% (w/v) to 10% (w/v), 10% (w/v) to 11% (w/v), 11% (w/v) to 12% (w/v), 12% (w/v) to 13% (w/v), 13% (w/v) to 14% (w/v), 14% (w/v) to 15% (w/v), 15% (w/v) to 16% (w/v), 16% (w/v) to 17% (w/v), 17% (w/v) to 18% (w/v), 18% (w/v) to 19% (w/v), 19% (w/v) to 20% (w/v), 20% (w/v) to 21% (w/v), 21% (w/v) to 22% (w/v), 22% (w/v) to 23% (w/v), 23% (w/v) to 24% (w/v), 24% (w/v) to 25% (w/v), 25% (w/v) to 26% (w/v), 26% (w/v) to 27% (w/v), 27% (w/v) to 28% (w/v), 28% (w/v) to 29% (w/v), 29% (w/v) to 30% (w/v), 30% (w/v) to 31% (w/v), 31% (w/v) to 32% (w/v), 32% (w/v) to 33% (w/v), 33% (w/v) to 34% (w/v), 34% (w/v) to 35% (w/v), 35% (w/v) to 36% (w/v), 36% (w/v) to 37% (w/v), 37% (w/v) to 38%, (w/v), 38% (w/v) to 39% (w/v), or 39% (w/v) to 40% (w/v).

The sealing fluid can further comprise a tissue-penetrating agent at about 1% (w/v) to about 40% (w/v). For example, the sealing fluid comprises a water a tissue-penetrating agent at about 1% (w/v) to 2% (w/v), 2% (w/v) to 3% (w/v), 3% (w/v) to 4% (w/v), 4% (w/v) to 5% (w/v), 5% (w/v) to 6% (w/v), 6% (w/v) to 7% (w/v), 7% (w/v) to 8% (w/v), 8% (w/v) to 9% (w/v), 9% (w/v) to 10% (w/v), 10% (w/v) to 11% (w/v), 11% (w/v) to 12% (w/v), 12% (w/v) to 13% (w/v), 13% (w/v) to 14% (w/v), 14% (w/v) to 15% (w/v), 15% (w/v) to 16% (w/v), 16% (w/v) to 17% (w/v), 17% (w/v) to 18% (w/v), 18% (w/v) to 19% (w/v), 19% (w/v) to 20% (w/v), 20% (w/v) to 21% (w/v), 21% (w/v) to 22% (w/v), 22% (w/v) to 23% (w/v), 23% (w/v) to 24% (w/v), 24% (w/v) to 25% (w/v), 25% (w/v) to 26% (w/v), 26% (w/v) to 27% (w/v), 27% (w/v) to 28% (w/v), 28% (w/v) to 29% (w/v), 29% (w/v) to 30% (w/v), 30% (w/v) to 31% (w/v), 31% (w/v) to 32% (w/v), 32% (w/v) to 33% (w/v), 33% (w/v) to 34% (w/v), 34% (w/v) to 35% (w/v), 35% (w/v) to 36% (w/v), 36% (w/v) to 37% (w/v), 37% (w/v) to 38%, (w/v), 38% (w/v) to 39% (w/v), or 39% (w/v) to 40% (w/v).

The sealing fluid can further comprise a water-soluble UV stabilizer at about 0.05 (w/v) to about 15% (w/v). For example, the sealing fluid comprises a water water-soluble UV stabilizer at about 0.05 (w/v) to 0.01 (w/v/), 0.01 (w/v/) to 1% (w/v), 1% (w/v) to 2% (w/v), 2% (w/v) to 3% (w/v), 3% (w/v) to 4% (w/v), 4% (w/v) to 5% (w/v), 5% (w/v) to 6% (w/v), 6% (w/v) to 7% (w/v), 7% (w/v) to 8% (w/v), 8% (w/v) to 9% (w/v), 9% (w/v) to 10% (w/v), 10%0/(w/v) to 11% (w/v), 11% (w/v) to 12% (w/v), 12% (w/v) to 13% (w/v), 13% (w/v) to 14% (w/v), or 14% (w/v) to 15% (w/v).

In another embodiment, the sealing fluid comprises about 8% (w/v) to about 10% (w/v) polyvinyl pyroliddone of about 40 kDa molecular weight.

In one embodiment, the sealing fluid comprises about 8% (w/v) to about 10% (w/v) polyvinyl pyroliddone of about 40 kDa molecular weight, and about 8% (w/v) to about 12% (w/v) ethanol, and has a viscosity of about 10 centipoise to about 20 centipoise at 20 degrees Celsius.

In another embodiment, the sealing fluid comprises about 8% (w/v) to about 10% (w/v) polyvinyl alcohol of about 40 kDa molecular weight.

In one embodiment, the sealing fluid comprises about 8% (w/v) to about 10% (w/v) polyvinyl alcohol of about 40 kDa molecular weight, and about 8% (w/v) to about 12% (w/v) ethanol, and has a viscosity of about 10 centipoise to about 20 centipoise at 20 degrees Celsius.

In another embodiment, the sealing fluid comprises about 8% (w/v) to about 10% (w/v) polyvinyl alcohol of about 27 kDa molecular weight.

In one embodiment, the sealing fluid comprises about 8% (w/v) to about 10% (w/v) polyvinyl alcohol of about 27 kDa molecular weight, and about 8% (w/v) to about 12% (w/v) ethanol, and has a viscosity of about 10 centipoise to about 20 centipoise at 20 degrees Celsius.

In another embodiment, the sealing fluid comprises about 8% (w/v) to about 10% (w/v) polyvinyl alcohol of about 185 kDa molecular weight.

In one embodiment, the sealing fluid comprises about 8% (w/v) to about 10% (w/v) polyvinyl alcohol of about 185 kDa molecular weight, and about 8% (w/v) to about 12% (w/v) ethanol, and has a viscosity of about 10 centipoise to about 20 centipoise at 20 degrees Celsius.

In another embodiment, the sealing fluid comprises about 8% (w/v) to about 10% (w/v) polyvinyl alcohol of about 200 kDa molecular weight.

In one embodiment, the sealing fluid comprises about 8% (w/v) to about 10% (w/v) polyvinyl alcohol of about 200 kDa molecular weight, and about 8% (w/v) to about 12% (w/v) ethanol, and has a viscosity of about 10 centipoise to about 20 centipoise at 20 degrees Celsius.

The sealing fluid is prepared by adding the polymer in dry form to water and mixing until dissolved.

Water-Soluble Dehydration Protectant

The sealing fluid, comprising a water-soluble dehydration protectant, infiltrates or penetrates the biological specimen. Use of the sealing fluid eliminates the step of dehydrating the stained biological specimen. The presence of the water-soluble dehydration protectant in the specimen also prevents drying artifacts that would typically occur in the absence of the water-soluble dehydration protectant.

A dehydration protectant is water soluble, optically transparent upon drying so as not to interfere with microscopic analysis, and is chemically inert with respect to a stain used to stain a specimen.

The dehydration protectant can be a water-soluble plasticizer. A plasticizer is a liquid (for example, a solvent) added to a synthetic resin to produce or promote plasticity or flexibility or to reduce brittleness. Plasticizers can be divided into water soluble and insoluble plasticizers. Water-soluble plasticizers are dissolved, while insoluble plasticizers have to be emulsified in the aqueous phase of the polymer dispersions. One or more water-soluble plasticizers can be used in a sealing fluid.

Exemplary dehydration protectants are polyvinyl alcohols such as Mowiol® 4-88, Mowiol 4-98, Mowiol 40-88, a high molecular weight polyvinyl alcohol, a low molecular weight polyvinyl alcohol, a high molecular weight polyvinylpyrrolidone, or a low molecular weight polyvinylpyrrolidone.

Mowiol® 4-88 (Aldrich) is a high quality anti-fade medium used for immunofluorescence. When Mowiol® 4-88 hardens it has the same refractive index as immersion oil. Mowiol® 4-88 is a solution of polyvinyl alcohol (PVA) and has a molecular weight of 31,000. Mowiol® 4-88 has a viscosity of 3.5-4.5 mPa·s, 4% in water at 20 degrees Celsius. Mowiol® 4-88 is a hydrophilic polymer. Other polyvinyl alcohols can also be used as a water-soluble dehydration protectant in the sealing fluids disclosed herein.

Polyvinyl Alcohols

Polyvinyl alcohols (PVAs) can also be used as a water-soluble dehydration protectant in the sealing fluids disclosed herein. Polyvinyl alcohols are polymers of vinyl alcohol. Polymers of vinyl alcohol cannot exist in a free form, therefore most polyvinyl alcohols have been manufactured by polymerization of vinyl acetate, which, unlike vinyl alcohol, is stable. The polyvinyl acetate produced then undergoes alcoholysis. The technical properties of polyvinyl alcohol depend on the molar mass and residual acetyl group content, therefore industrial manufacturing processes are designed to ensure exact adherence to these two parameters.

Mowiol is the trade name of polyvinyl alcohols marketed by Clariant. These polyvinyl alcohols are manufactured from polyvinyl acetate by alcoholysis using a continuous process. By varying the degree of polymerization of the polyvinyl acetate and its degree of hydrolysis several different grades can be made. These grades are supplied in the form of fine granules. Several different grades of Mowiol® and their molecular weights are provided below in Table 1 and Table 2.

TABLE 1

Partially Hydrolyzed Grades of Mowiol®

| Mowiol 15-79 | 100,000 |
| Mowiol 3-83 | 14,000 |
| Mowiol 4-88 | 31,000 |
| Mowiol 5-88 | 37,000 |
| Mowiol 8-88 | 67,000 |
| Mowiol 18-88 | 130,000 |
| Mowiol 23-88 | 150,000 |
| Mowiol 26-88 | 160,000 |
| Mowiol 40-88 | 205,000 |
| Mowiol 47-88 | — |
| Mowiol 30-92 | 175,000 |

TABLE 2

Fully Hydrolyzed Grades of Mowiol®

| Mowiol 3-98 | 16,000 |
| Mowiol 4-98 | 27,000 |
| Mowiol 6-98 | 47,000 |
| Mowiol 10-98 | 61,000 |
| Mowiol 20-98 | 125,000 |
| Mowiol 56-98 | 195,000 |
| Mowiol 28-98 | 145,000 |

Polyvinylpyrrolidones

Polyvinylpyrrolidones (PVPs) can also be used as a water-soluble dehydration protectant in the sealing fluids disclosed herein. Exemplary PVPs are discussed in, "PVP Polyvinylpyrrolidone Polymers—Intermediates, solvents, monomers, polymers, and specialty chemicals," by Ashland®, as described below.

PVP polymers are available in several viscosity grades, ranging from low to high molecular weight. This range, coupled with solubility in aqueous and organic solvent systems combined with its non-toxic character, gives PVP great flexibility. PVP polymer is supplied in five viscosity grades as a powder and/or aqueous solution. Exemplary PVPs and their molecular weight (MW) ranges are provided below in Table 3; all are sold by Ashland®.

TABLE 3

| Name | MW Range (measured by LALLS) |
|---|---|
| PVP K-15 | 6,000-15,000 |
| PVP K-30 | 40,000-80,000 |
| PVP K-60 | 240,000-450,000 |
| PVP K-90 | 900,000-1,500,000 |
| PVP K-120 | 2,000,000-3,000,000 |

Polyvinylpyrrolidone can be prepared to yield products with a variety of molecular weights dependent upon the methods used to synthesize the polymer. The product so obtained has a molecular weight range from 2,500 to 2,900,000. Since the polymer consists of a series of different chain length polymers, the molecular weight is expressed as an average of the various molecular weights of the different chain length units that comprise the polymer.

There have been several studies that have been devoted to the determination of the molecular weight of PVP. The low molecular weight polymers have narrower distribution curves of molecular entities than the higher molecular weight compounds. Some of the techniques for measuring the molecular weight of various PVP products are based on measuring sedimentation, light scattering, osmometry, NMR spectroscopy, ebulliometry, and size exclusion chromatography for determining absolute molecular weight distribution. By the use of these methods, any one of three molecular weight parameters can be measured, namely the number average (Mn), viscosity average (Mv), and weight average (Mw). Each of these characteristics can yield a different answer for the same polymer as illustrated by using these measurement techniques in the analysis of the same PVP K-30 sample. The results for PVP K-30 are: number average (Mn)—10,000; viscosity average (Mv)—40,000; weight average (Mw)—55,000. Conventionally, molecular weights are expressed by their K-values, which are based on kinematic viscosity measurements.

PVP properties include: linear nonionic polymer; high polarity/proton acceptor; amphiphilic; compatible with a variety of resins and electrolytes; soluble in water and polar solvents, insoluble in esters, ethers, ketones and hydrocarbons; hard, glossy, transparent, oxygen permeable films which adhere to a variety of substrates; hygroscopic; adhesive and cohesive properties; cross-linkable; and physiologically inert.

Water-Soluble Plasticizers

If a water-soluble dehydration protectant that is used in a sealing fluid described herein is brittle, an optional water-soluble plasticizer can be added to the sealing fluid.

Exemplary water-soluble plasticizers that can be added to a sealing fluid already comprising a water-soluble dehydration protectant are: polyethylene glycol (PEG); triethyl citrate (TEC); triacetin; glycerol; polyethylene glycol; triacetin; triethyl citrate; and diethyl phthalate; carboxymethylcellulose; cellulose acetate; cellulose acetate propionate; dibutyl tartrate; diethylene glycol; dimethyl phthalate; dytol B-35, J-68 and L-79 ® (aliphatic alcohol (mixture of C12, C14 and C16), dodecyl alcohol and lauryl alcohol); 2-ethyl-1,3 hexanediol; glycerin; glyceryl monoricinoleate; hyprin GP-25 ® (tris-1,2,3-hydroxypropoxypropane and bis(hydroxypropoxy)hydroxy propane); Igepal CO-430 ® (Nonyl Phenol Ethoxylate, 4EO); Lorol® (Fatty Alcohol)); oleyl alcohol; Resoflex R-363 ®; Santicizer 141, B16, and E-35 ®; Santolite MHP® (4-Toluenesulfonamideformaldehyde resin); Shellac; and Sorbitol.

Tissue Penetrating Agent

A tissue-penetrating agent, such as an alcohol may be added to the sealing fluid prior to infiltrating the specimen, to facilitate tissue penetration. A tissue-penetrating agent at about 1% (w/v) to about 40% (w/v) can be added to the sealing fluid. A tissue-penetrating agent is able to enter, pass through, diffuse into, or infiltrate the specimen.

Exemplary tissue-penetrating agents are: an alcohol, methanol, propanol, isopropanol, ethanol, ethyl alcohol, ethanol, glycerol, a glycerol polymer, polyethylene glycol, butanol, pentanol, propylene glycol, ethylene glycol, a monohydric alcohol, a dihydric alcohol, or a polyhydric alcohol.

Water-Soluble Ultraviolet Stabilizers

Photochemical processes that convert ultra violet (UV) photons into free radicals or other harmful reactive chemical species (e.g. singlet oxygen, or hydroxyl radical) can react with stains causing the stains to fade over time. Typically stained microscope slides are stored in the dark to minimize the fading effect of UV radiation. However, over long periods of time, including occasional removal of the slides from storage for review, significant fading can occur.

The sealing fluids disclosed herein can comprise one or more water-soluble UV stabilizers that help reduce the fading effects of UV radiation. Water-soluble UV stabilizers that can be used in the sealing fluids disclosed herein can be ultraviolet (UV) absorbers, quenchers, or hindered amine light stabilizers (HALS).

UV Absorbers

UV absorbers are a type of light stabilizer that function by competing with chromophores to absorb UV radiation. UV absorbers change harmful UV radiation into harmless infrared radiation or heat that is dissipated through a polymer matrix.

Carbon black is a commonly used UV absorber. Another UV absorber is rutile titanium oxide, which is effective in the 300-400 nm range, but is not as useful below 315 nm. Hydroxybenzophenone and hydroxyphenylbenzotriazole are also well known UV absorbers that are suitable for neutral or transparent applications. Other UV absorbers include oxanilides for polyamides, benzoates, benzophenones for PVC, and benzotriazoles and hydroxyphenyltriazines for polycarbonate. Another UV absorber is 2-phenylbenzimidazole-5-sulfonic acid. A UV absorber can be any UV absorber that is water-soluble, transparent upon drying, and chemically inert with respect to stains. A UV absorber can absorb in a range of less then about 310 millimicrons. One or more UV absorbers can be used in the sealing fluids disclosed herein.

A UV absorber can be a 2-hydroxybenzophenone (including a salicylate), a 2-hydroxyphenylbenzotriazole, and a substituted acrylonitrile. These three groups are both strong UV absorbers and stable to long exposure to UV light (at least several hundred hours in the Fadeometer). A UV absorbers can be a: 2, 4 dihydroxy-; 2, 2', 4, 4' tetrahydroxy-; 2 hydroxy, 4, methoxy-; 2, 2'dihydroxy 4, 4', dimethoxy-; 2 hydroxy, 3, 5 dicholoro-; and a 2 hydroxy, 4 methoxy, 5 sulfo-.

Quenchers

Quenchers return excited states of chromophores to ground states by an energy transfer process. The energy transfer agent functions by quenching the excited state of a carbonyl group formed during the photo-oxidation of a plastic material and through the decomposition of hydroperoxides. This quenching prevents bond cleavage and ultimately the formation of free radicals. An exemplary quenchers is a nickel quencher.

Hindered Amine Light Stabilizers (HALS)

HALS are long-term thermal stabilizers that act by trapping free radicals formed during the photo-oxidation of a plastic material and thus limiting the photodegradation process. The ability of Hindered Amine Light Stabilizers to scavenge radicals created by UV absorption is explained by the formation of nitroxyl radicals through a process known as the Denisov Cycle. Although there are wide structural differences in the HALS products commercially available, all share the 2,2,6,6-tetramethylpiperidine ring structure. HALS are proficient UV stabilizers for a wide range of plastics. HALS are very effective stabilizers in polyolefins, polyethylene and polyurethane.

Exemplary HALS that can be used in the sealing fluids disclosed herein are provided in Table 4 and Table 5 below:

TABLE 4

| HALS used in plastics, coatings, and cosmetics | Exemplary Effective Concentration |
| --- | --- |
| substituted benzophenones | 0.1-0.3% |
| 2-phenylbenzimidazole-5-sulfuric acid | 5-10% |
| benzotriazole | 1-3% |
| benzoate | 0.1-1% |
| a compound with a 2,2,6,6-tramethlypiperidine ring | 0.1-0.3% |

TABLE 5

| HALS used in sunscreens | Maximum Concentration (%) | Absorbance UVA: 315-400 nm UVB: 280-315 nm |
|---|---|---|
| Aminobenzoic acid | 15 | UV-B |
| Avobenzone | 3 | UV-A I |
| Cinoxate | 3 | UV-B |
| Dioxybenzone | 3 | UV-B, UV-A II |
| Ecamsule | 2 | UV-A II |
| Ensulizole | 4 | UV-B |
| Homosalate | 15 | UV-B |
| Meradimate | 5 | UV-A II |
| Octocrylene | 10 | UV-B |
| Octinoxate | 7.5 | UV-B |
| Octisalate | 5 | UV-B |
| Oxybenzone | 6 | UV-B, UV-A II |
| Padimate O | 8 | UV-B |
| Sulisobenzone | 10 | UV-B, UV-A II |
| Titanium dioxide | 25 | Physical |
| Trolamine salicylate | 12 | UV-B |
| Zinc oxide | 25 | Physical |

As all three water-soluble UV stabilizers described above, function by different mechanisms, they are often combined into synergistic UV absorbing additives. For example, benzotriazoles are often combined with HALS to protect pigmented systems from fading and color changes. Any one or more of the water-soluble UV stabilizers described above can be used individually or in combination in the sealing fluids disclosed herein.

Specimen/Sample

The words "specimen" and "sample" are used interchangeably throughout the disclosure. A specimen can be a biological specimen. A specimen can be one or more cells, a mixture of different types of cells, or a population of cells. A specimen can comprise eukaryotic or prokaryotic cells or a mixture of both. A specimen, such as a group of cells, can be grown directly on a surface suited for cell culture (e.g. a tissue culture dish) or loose cells can be applied to a surface, for example, a microscope slide. A specimen can be a tissue sample or a portion or slice of a tissue sample. A specimen can be embedded in a matrix, such as paraffin, or may be freshly frozen after collection from a mammal (e.g. human or animal).

Staining

Staining is a technique used in microscopic analysis to enhance contrast in the microscopic image. Stains and dyes can be chemical compounds or biological molecules. A stains or dye can be tagged, conjugated to, or be labeled with another chemical compound. Stains and dyes are often used to highlight structures in biological tissue samples to define and examine particular tissue structures, cell populations, or organelles within individual cells. Stains and dyes may also be specific to particular DNA, proteins, lipids, or carbohydrates present in the specimen, and help to determine the presence or absence, or the quantity of the particular species of interest.

The term "staining" refers to a formation of specific binding interaction between the stains or the dyes to the species of interest. For example, a staining may occur when a biomarker, such as an antibody, specifically binds to a protein or an antigen; when a nucleic acid binds to a DNA or RNA sequence; or when a chemical compound that specifically recognizes the nucleus of a cell producing a visible color upon the subsequent contact of a substrate.

Compatibility Between Stains and Solvents

It is important to protect the stained specimen from dissolving after exposure to a solvent. Typically stains for biological samples are selected specifically because of their resistance to organic solvents such as those that might be encountered during dehydration and mounting. Exemplary solvents are: alcohols, xylene, toluene, d-limonene, and other aliphatic hydrocarbons. However the requirement for compatibility between stains and solvents greatly limits the choice of stains that might otherwise be useful in staining a specimen. The sealing fluids disclosed herein can be used with any stain, regardless of the stain's compatibility with an organic solvent.

Organic Solvents

Exemplary organic solvents are any alcohol, xylene, and toluene. Other exemplary organic solvents are: acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol dimethyl ether), 1,2-dimethoxyethane (glyme, DME), dimethyl-formamide (DMF), dimethyl sulfoxide (DMSO), 1,4-dioxane, ethanol, ethyl acetate, ethylene glycol, glycerin, heptane, Hexamethylphosphoramide (HMPA), Hexamethylphosphorous triamide (HMPT), hexane, limonene, methanol, methyl t-butyl ether (MTBE), methylene chloride, N-methyl-2-pyrrolidinone (NMP), nitromethane, pentane, Petroleum ether (ligroine), 1-propanol, 2-propanol, pyridine, tetrahydrofuran (THF), triethyl amine, water, o-xylene, m-xylene, or p-xylene.

Dyes/Stains

The terms "dye" and "stain" can be used interchangeably throughout the disclosure. A dye/stain can also be a chromogen.

Dyes demonstrate an affinity for molecules or organisms within cells and tissues. For example, a dye (stain) can be specific to connective tissue, erythrocytes, mitochondria, nucleic acids, collagen, reticulum, muscle, plasma, nuclei, bacteria, nerve cells, liver cells, cell walls, pituitary cells, reticulum, bone, cartilage, pancreatic cells, marrow cells, cytoplasm, parasites, keratin, or any portion or combination of any of the above. Other examples of dye specificity are provided below in Table 6 and Table 7.

The affinity of dyes for elements that are present in a cell or tissue is affected by several factors: the structure of the dye molecule; the shape of the dye molecule; the charge distribution of the dye; and solvent characteristics.

Stains can be used on fixed, or non-living cells.

The mounted specimens described herein can be stored for re-evaluation over a period of months or even years. Use of the disclosed sealing fluids prevents fading of the stained specimen. The sealing fluid provides a layer separating the stained biological specimen from the organic solvents present in the mounting medium. This barrier provides anti-fade characteristics of the sealing fluid of the present disclosure.

Any stain can be used in combination with the sealing fluids disclosed herein. A dye can be an acidophilic stain or a basophilic stain. Numerous dyes are available. Provided herein are exemplary dyes that can be used in combination with the disclosed sealing fluids.

Exemplary dyes are: Acridine Orange stain, Auramine-Rhodamine stain, Calcofluor White stain, a capsule stain, a cytoplasmic inclusion stain, an endospore stain, a gram stain, and a flagella stain. Other exemplary dyes are: Acid Fuchsin, Acridine Orange, Alcian Blue 8GX, Alizarin Red S, Aniline Blue, Auramine O, Azocarmine G, Azur A, Azur B, Azur II, Basic Fuchsin (Rosaniline), Basic Green 4 (Malachite Green), Biebrich Scarlet (Ponceau BS), Bismarck Brown Y, Brilliant Cresyl Blue, Carmine (Alum Lake), Cresyl Fast Violet, (Cresyl Violet Acetate), Crystal Violet, Eosin Y, Erythrosin B (Erythrosin extra bluish), Fluorescein Isothiocyanate, Giemsa, Hematoxylin, Indigo Carmine, Light Green SF-Yellowish, Methyl Green, Methylene Blue, Methyl Violet 2B, Nigrosin—W. S., Nile Blue A, Oil Red O, Orange II, Orange G, Phloxine B, Pyronin Y, Safranin O, Sudan Black B, Toluidine Blue O, and Wright stain. Additional exemplary dyes are Papanicolaou stains and chemical stains. An exemplary chemical stain is haematoxylin and eosin (H&E). Other exemplary dyes are: Bismarck Brown, Carmine, Coomassie blue, Crystal violet, DAPI, Eosin, Ethidium bromide, Fuchsin, Hoechst stains, Iodine, Malachite green, Methylene blue, Neutral/Toluene red, Nile blue, Nile red/Nile blue oxazone, Osmium tetroxide, Rhodamine, and Safranin.

Other exemplary stains that can be used with the aqueous sealing fluids disclosed herein are found in Conn's Biological Stains, 10th edition, 2002.

In addition, the Biological Stain Commission (BSC) ensures the quality of a dye through independent testing of the dye according to appropriately rigorous chemical and performance criteria. The BSC then certifies the dyes and the certification labels can be attached to the containers used by companies marketing the certified dyes to assure consumers that these dyes have met the performance criteria of the Biological Stain Commission. The testing methods and requirements for certification are described in Penney D P, Powers J M, Frank M, Willis C, Churukian C (2002) Analysis and testing of biological stains—The Biological Stain Commission Procedures. Biotech. Histochem. 77: 237-275. Numerous dyes have been certified by the BSC. Any dye that is certified by the BSC can be used with the aqueous sealing fluids described herein. Exemplary dyes are listed in the first column of Table 6 provided below. In the second column, the certified use is listed.

TABLE 6

Exemplary Dyes for use with the Disclosed Sealing Fluids

| Dye | Use |
|---|---|
| Acid Fuchsin | Histology, Andrade Indicator |
| Alcian Blue 8GX | Histology |
| Alizarin Red S | Staining Bone |
| Aniline Blue, W.S/Methyl Blue | Histology |
| Auramine O | Fluorescent Microscopy |
| Azocarmine G/B | Histology |
| Azure A | Histology, Compounding Of Blood Stains |
| Azure B | Histology, Compounding Of Blood Stains |
| Azure C | Histology |
| Basic Fuchsin | Histology, Feulgen Reaction, Bacteriology Stain |
| Basic Fuchsin, Flagella | Special for Flagella Staining |
| Bismarck Brown Y | Histology, Bacteriology (Staining) |
| Brilliant Cresyl Blue | Supravital Staining (Blood) |
| Brilliant Green | Bacteriology (Media Stain) |
| Carmine | Histology |
| Chlorazol Black E | Histology, Cytology |
| Celestine Blue B | Histology, Cytology |
| Congo Red | Histology |
| Cresyl Violet Acetate | Histology |
| Crystal Violet | Histology, Cytology, Bacteriology (Media Stain) |
| Darrow Red | Histology |
| Eosin B | Histology |
| Eosin Y | Histology, Compounding of Blood Stains |
| Erythrosin B | Histology |
| Ethyl Eosin | Histology |
| Fast Green FCF | Histology, Cytology |
| Fluorescein Isothiocyanate | Immunofluorescence |
| Giemsa Stain | Blood Staining |
| Hematoxylin | Histology, Cytology |
| Indigo Carmine | Histology |
| Janus Green B | Supravital Staining (Blood) |
| Jenner Stain | Blood Smear |
| Light Green SF Yellowish | Histology, Cytology |
| Malachite Green | Histology, Bacteriology (Staining) |
| Martius Yellow | Histology |
| Methyl Green | Histology, Compounding of Pappenheim Stain |
| Methyl Orange | Histology |
| Methyl Violet 2B | Histology |
| Methylene Blue | Histology, Bacteriology Stain, Compounding of Blood Stains |
| Methylene Violet | Compounding of Blood Stains |
| Neutral Red | Supravital Staining (Blood) |
| Nigrosin | Bacteriology (Staining) |
| Nile Blue A | Histology |
| Oil Red O | Fat Staining |
| Orange G | Histology |
| Orange II | Histology |
| Orcein, Synthetic | Histology, Cytology |
| Pararosaniline (Basic Fuchsin) | Histology, Feulgen Reaction, Bacteriology Stain |
| Phloxine B | Histology |
| Protargol S | Staining Nervous Tissue |
| Pyronin B | Histology |
| Safranin O | Histology, Cytology, Bacteriology (Staining) |
| Sudan Black B | Fat Staining |
| Sudan III | Fat Staining |
| Sudan IV | Fat Staining |
| Tetrachrome Stain | Blood Staining |
| Thionin | Histology |
| Toluidine Blue O | Histology |
| Wright Stain | Blood Staining |

Other exemplary dyes and their uses are provided in the Table 7 below. The dyes in Table 7 below can be purchased from Electron Microscopy Sciences, USA.

TABLE 7

| Dye | Use |
|---|---|
| Acid Fuchsin | Stain for connective tissue and erythrocytes; and proteinaceous material in liver. Cain's method for mitochondria |
| Acridine Orange | Pickett's fluorescence method for fungi fluorescent against a dark background. For differentiation of nucleic acids and cytology |
| Alcian Blue 8GX | Acid mucopolysaccharides. Cell walls. Cartilage granules. As a carbohydrate and mucosubstance stain in different pH levels. Movat's method for connective tissue stain. Monroe/Frommer method for pituitary staining. AB/PAS/OG method for human adenohypophyseal cytology |
| Alizarin Red S | Minute bone and fetal ossification in mammalian embryos. Used with toluidine blue for distinction of bone and cartilage in mammalian embryos. Used with alizarin red for calcium deposits. |
| Aniline Blue | Used with Biebrich scarlet for staining collagen, reticulum, muscle, plasma, and nuclei. All connective tissues. Used as a counterstain with red nuclear dye. |

TABLE 7-continued

| | |
|---|---|
| Auramine O | Staining paraffin sections of infected tissue. Acid-fast organisms exhibit fluorescence. |
| Azocarmine G | Alpha, beta, and all D-cells of the islets of Langerhans and in all animals. |
| Azur A | A nuclear stain. Cell granules McNeal method for leukocytes. |
| Azur B | Distinction of cellular RNA and DNA in botanical tissue. Negri body stain. Malarial parasites |
| Azur II | Morphological details of marrow cells, nuclei, and bacteria. |
| Basic Fuchsin (Rosaniline) | Gram positive/negative bacteria. A pituitary stain. |
| Basic Green 4 (Malachite Green) | In microbiology, distinction of diphtheria and other bacteria. A vital stain for onion epidermis. |
| Biebrich Scarlet (Ponceau BS) | Used with picric acid/aniline blue for staining collagen, reticulum, muscle, and plasma. Luna's method for erythrocytes and eosinophil granules. Guard's method for sex chromatin and nuclear chromatin. |
| Bismarck Brown Y | PAP for staining smears. Nuclei and granules. Mucin and calciform cells of intestine, cartilage and embryo. |
| Brilliant Cresyl Blue | Platelets and reticulum of immature red cells. Counterstained with Wright's stain. |
| Carmine (Alum Lake) | Glycogen stain. Elastic fibers in blood vessels, nuclei, and collagen. |
| Cresyl Fast Violet, (Cresyl Violet Acetate) | Vogt's method for nerve cells. A neurological tissue stain. Nissl substance and PAS-positive material. Powers and Clark method for spinal cord and brain with formalin or Bouins fixed. |
| Crystal Violet | Gram positive/Gram negative bacteria, and filaments. Holzer's method for glial fibers (nerve). Amyloid in pathological human tissue. |
| Eosin Y | Maximow's method for morphological details of marrow cells; a constituent of Wright Stain for elastic fibers in blood; as a eosin-phloxine counterstain. |
| Erythrosin B (Erythrosin extra bluish) | Used with methylene blue as a plasma stain for nerve cells. |
| Fast Green FCF | Lillie modification of Masson's for cells, cytoplasm, muscle, and collagen; Guard method for sex chromatin. |
| Fluorescein Isothiocyanate | Culing's Method for fluorescent antibody staining for demonstration of specific antigens. |
| Giemsa | Thin film stain for differentiation of types of leucocytes; *Rickettsiae*, bacteria, and inclusion bodies. May-Grunwald/Giemsa for bone marrow stain. Pinkus' acid orcein-giemsa for connective tissue staining. |
| Hematoxylin | Weige's iron hematoxylin for nuclear stains. Gill's hematoxylin for nuclei and nuclear chromatin. |
| Indigo Carmine | A stain for Negri bodies; used with acid fuchsin. Used in picric acid in contrast to basic fuchsin. |
| Light Green SF, Yellowish | Grocott's method for fungi. Dahl's method as a bone and calcium stain. McManus' method for glycogen. Fraser-Lendrum method as a connective tissue stain. |
| Methyl Green | Myeloperoxidase stain; Used with bismarck brown for mucin and calciform cells of intestine, cartilage of trachea, and embryonic tissue; Used with toluidine blue for differentiating between diphtheria and other bacteria. |
| Methylene Blue | For use in acid-fast bacteria, acid-fast bacilli, and as a *rickettsia* stain. Cain's method for mitochondria. For staining Negri bodies in nerve cells. |
| Methyl Violet 2B | Highman's method for amyloid and nuclei staining. Used with crystal violet and bismarck brown Y for staining metachromatic granules of diphtheria organisms. |
| Nigrosin, W.S. | For staining the central nervous system. For the negative staining of bacteria; used in place of India ink. |
| Nile Blue A | A fat and lipid stain; differentiation of melamines and lipofuchsins. Staining for phospholipids. |
| Oil Red O | Used as a pigment stain. |
| Orange II | Kalter's method used with fast green FCF, safranin O, and crystal violet for quadruple staining of tissues. Orange G substitution for better contrast. |
| Orange G | For staining fibrin, keratin, collagen, and erythrocytes. Staining alpha, beta, and gamma cells. For staining nissl substances and PAS-positive material. |
| Phloxine B | For staining inclusion bodies and nuclei. Thomas's method for malarial parasites. For staining hemoglobin and hemosiderin. For staining keratin, prekeratin and mucin. A beta cell stain Counterstain for hematoxylin. |
| Pyronin Y | Cudder's method combined Gram/Pappenheim stain for gonorrheal pus. Kurnick's method used with methyl green which stains liver cells. For staining protein in the diazosulfanilic acid technique; a substitute for azur A. Can be used for pyronin B. |

TABLE 7-continued

| | |
|---|---|
| Safranin O | Prussian Blue method for hemosiderin. Weige's iron hematoxylin with methachromic dyes which stain nuclei and granules. A alkaline phosphate stain. Flemming's method for staining chromatin and nuclear elements. |
| Sudan Black B | A stain for fat in animal tissue. A stain for chromosomes, golgi, and leucocyte granules. |
| Toluidine Blue O | Alizarin red/Toluidine blue for distinction between bone and cartilage and the degree of ossification in mammalian embryos. Johnson's method for metachromatic tissue. With cresyl violet for staining DNA and RNA. With thionin for malignant cells of biopsy specimens. |
| Wright Stain | For differentiation of blood corpuscles. Used with brilliant cresyl blue for staining platelets and reticulum of immature red cells. For staining blood and bone marrow films. |

Chromogen

A chromogen is a substance capable of conversion into a pigment or dye (a stain). A chromogen begins as a colorless compound that is converted to a colored compound during the staining process by an enzymatic reaction. A chromogen can be mixed with a substrate. The chromogen/substrate mixture is then converted by an enzymatic reaction to a colored compound.

Any chromogen can be used in combination with the disclosed sealing fluids. For example, a chromogen used in an immunohistochemistry (IHC) or an in situ hybridization (ISH) assay can be used in combination with the disclosed sealing fluids.

Typically the enzymes horseradish peroxidase (HRP) or alkaline phosphatase (AP) are used with an appropriate chromogen/substrate to produce a reaction product that can generally be visualized using light microscopy. For example, HRP (enzyme) can be used with a chromogen and a substrate (hydrogen peroxide). Alternatively, AP (enzyme) can be used with a chromogen and a substrate (naphthol-phosphate). Other peroxidases and phosphatases can also be used. Any chromogen that uses either Horseradish Peroxidase (HRP), Peroxidase, or Alkaline Phosphatase (AP), or phosphatase as an enzyme label can be used with the disclosed sealing fluids.

Exemplary chromogens are: 3,3',5,5', tetramethylbenzidine (TMB); 3,3'-diaminobenzidine; Fast Red TR; New Fuchsin; PermaBlue; PermaGreen; PermaYellow; PermaBlack; PermaRed; Benzidine; 3-Amino-9-ethylcarbazole; Variamine Blue; Fast Blue BB; Basic Fuchsin; New Fucsin; Pararosanaline; Indoxyl phosphates; 6-Chloro-3-indoxyl phosphate; 5-Bromo-4-chloro-3-indoxyl phosphate; 3-indoxyl phosphate; a tetrazolium, Nitro blue tetrazolium; Tetranitro blue tetrazolium; or Iodonitro tetrazolium.

Mounting

Mounting is attaching a specimen or sample to a structure, such as a glass microscope slide, for observation. Cells may either be grown directly on the slide or loose cells can be applied to a slide. Thin sections (slices) of material such as tissue may also be applied to a microscope slide for observation.

General Description of a Mounting Process Using the Sealing Fluids of the Disclosure The final step before microscopic analysis is the mounting of the slide (containing the stained biological specimen) to improve its optical resolution. The sealing fluids disclosed herein are used in this step. A general mounting process is described below. One of skill in the art could easily change the times described below based on the specific stain and specimen.

Stained slides are removed from their staining solutions and rinsed with water. The stained slides are then submerged in sealing fluid for a length of time sufficient to allow penetration into the tissue, generally about five minutes is sufficient for this penetration. The stained slides can be submerged in sealing fluid for about 1 minute to about 10 minutes. Alternatively, the slides can be laid out horizontally and covered with sealing fluid. Using this alternative method, the slides can be covered (incubated) for about 5 minutes, and then the sealing fluid can be drained off of the slide. The slides are then allowed to dry, for example, in a vertical position such that excess sealing fluid drains off the slides, thus facilitating drying. This drying step usually takes between about 15 to about 30 minutes. A mounting medium, such as a permanent mounting medium, is then applied to the dried slides, and a glass coverslip is overlaid the mounting medium. The mounted slides are then typically allowed to dry before microscopic examination.

Mounting Media

A review of mounting media is provided by Ravikumar S, Surekha R, Thavarajah R. Mounting media: An overview. J NTR Univ Health Sci 2014; 3:S1-8, and disclosed below. Biological specimens that need to be examined for any length of time or to be stored must be mounted under a cover-slip. There are various types of mounting media available for mounting tissue sections. Some types of mounting media harden to hold the coverslip firmly in place and other types use different solvents such as water, glycerin and xylene because the stains in the sample preparation are sensitive to a particular solvent. In order to prevent the quenching of immonofluorescent slides, few mounting media contain antifade reagents.

Mounting medium is a solution in which the specimen is embedded, generally under a cover glass. It may be liquid, gum or resinous, soluble in water, alcohol or other solvents and be sealed from the external atmosphere by non-soluble ringing media. The main purpose of mounting media is to physically protect the specimen; the mounting medium bonds specimen, slide and coverslip together with a clear durable film. The medium is important for the image formation as it affects the specimen's rendition.

Mounting media should have a refractive index (RI) as close as possible to that of the fixed protein (tissue) (approximately 1.53). A mounting medium with an RI close to that of the fixed tissue (specimen) will render it transparent, with only the stained tissue elements visible. A mounting medium with an RI too far on either side of 1.53 will provide poor clarity and contrast. A mounting medium can be chosen that will not fade the particular stain(s) used.

There are two classes of mounting media: resinous mounting media (hydrophobic/adhesives/organic/non-aqueous) and aqueous mounting media (hydrophilic/non-adhesive).

Resinous Mounting Media

The phrases resinous mounting medium and resin-based mounting medium can be used interchangeably herein. Resinous mounting media are natural or synthetic resins dissolved in, for example, benzene, toluene, or xylene. Resinous mounting medium are also called organic mounting medium or permanent mounting medium. They generally contain an organic solvent such as toluene, benzene, or xylene. Resinous mounting media are generally preferred because they offer better optical resolution and preserve the stains better.

Resinous mounting medium can have a refractive index of about 1.5 to about 1.6. Exemplary resinous mounting medium that can be used in combination with the disclosed sealing fluids, along with the RI of the media are as follows: Canada balsam (RI=1.52-1.54); phenol balsam (a variant of Canada balsam); Dammar balsam (RI=1.52-1.54) Euparal (RI=1.48); DPX (DePeX [Distrene 80: a commercial polystyrene, a plasticizer, e.g., dibutyl phthalate and xylene]) (RI=1.52); Gurr's neutral mounting medium (RI=1.51); Permount (RI=1.526); Pro-texx (RI=1.495); Technicon Resin (RI=1.62); Uv-inert (RI=1.517); XAM (RI=1.52); (Fisher Scientific); Histomount, R.I. 1.50 (Thermo-Fisher); Coverbond, RI 1.53 (VWR International); and Histoclad R.I. 1.54 (Becton-Dickenson).

Aqueous Mounting Media

The phrases aqueous mounting medium and aqueous-based mounting medium can be used interchangeably herein. Aqueous mounting medium are used for mounting sections from distilled water when the stains would be decolorized or removed by alcohol and xylene as would be the case with most of the fat stains (e.g. Sudan methods). These media are of three types: the syrups, gelatin media, and Gum Arabic media. Aqueous mounting medium does not require tissue dehydration before mounting. Aqueous mounting media are generally intended as a final mounting media. It is applied to the slides while wet and then coverslipped with a glass coverslip.

Aqueous mounting medium can have a refractive index (RI) in the range of about 1.4 to about 1.52. Exemplary aqueous mounting medium that can be used with the sealing fluids disclosed herein, and their RIs, are as follows: 75% glycerol, RI 1.44 (Sigma-Aldrich); Vectashield, RI 1.46 (Vector Labs); Fluoromount, RI 1.40 (Sigma-Aldrich); glycerine jelly (RI=1.47); glycerine-glycerol (RI=1.47); Apathy's medium (RI=1.52); Farrant's medium (RI=1.43); Highman's medium (RI=1.52); fructose syrup (RI=1.47); polyvinyl alcohol (RI=1.5); and aqueous glycerol (RI=1.46)

The sealing fluid disclosed herein does not act as a mounting medium. It is less viscous and does not sufficiently cover the tissues to a depth that would be required for mounting a coverslip. Rather, the sealing fluid is designed to provide a thin layer that provides a barrier to subsequent exposure to solvents and mounting media. Furthermore, the sealing fluid is expected to be mounted over with a conventional mounting medium such as a permanent mounting medium described above.

Chemically Inert

A substance is chemically inert with a second substance if it is not chemically reactive with the second substance. A substance is chemically inert with a second substance if it has limited chemically reactivity with the second substance. An element is chemically inert if it is not readily reactive with other elements; forming few or no chemical compounds.

The sealing fluids of the disclosure are chemically inert with any stain for staining a specimen, including the stains described herein.

Hydrated

A specimen is considered hydrated when it contains more than about 25% (w/v) water. A specimen can be hydrated or a stained specimen can be hydrated. After staining, the stained specimen can be rinsed with water or any aqueous solution to become a hydrated stained specimen.

Solubility

Solubility is the susceptibility of being dissolved in or as if in a liquid, for example, water. Solubility is the maximum quantity of a substance that may be dissolved in another. In other words, the maximum amount of solute that may be dissolved in a solvent. A substance may be partially soluble if it is partly, but not completely, dissolved in a solvent within a given period of time. Soluble can be partially soluble, fully soluble, or any value in between partially soluble to fully soluble.

Exemplary solubility units include g/L (grams of solute per liter of solution) and m/L (moles of solute per liter of solution). Solubility can also be expressed in grams of solute per 0.2 lb (100 g) of solvent (e.g. water). Solubility units express the maximum amount of solute that will dissolve in either a given amount of solvent, or a given amount of solution, at a specific temperature.

Viscosity

Viscosity is a measure of the resistance of a fluid to deformation under shear stress. It is commonly perceived as "thickness", or resistance to pouring. Viscosity describes a fluid's internal resistance to flow and may be thought of as a measure of fluid friction.

The viscosity of the sealing fluid should be relatively low (e.g. 5,000 centipoise at 20 degrees Celsius) so that the sealing fluid can penetrate (or enter into) the specimen (tissue) effectively, the excess can then be drained from the slide and dried. The viscosity of the sealing fluid should be less than currently used mounting media, for example, resinous mounting media that have a higher viscosity. A sealing fluid of the present disclosure can have a viscosity of, for example, less than about 5,000 centipoise at 20 degrees Celsius. A sealing fluid of the present disclosure can have a viscosity of, for example, from 10 to 20 centipoise at 20 degrees Celsius, from 20 to 30 centipoise at 20 degrees Celsius, from 30 to 40 centipoise at 20 degrees Celsius, from 40 to 50 centipoise at 20 degrees Celsius, from 50 to 60 centipoise at 20 degrees Celsius, from 60 to 70 centipoise at 20 degrees Celsius, from 70 to 80 centipoise at 20 degrees Celsius, from 80 to 90 centipoise at 20 degrees Celsius, from 90 to 100 centipoise at 20 degrees Celsius, from 100 to 200 centipoise at 20 degrees Celsius, from 200 to 300 centipoise at 20 degrees Celsius, from 300 to 400 centipoise at 20 degrees Celsius, or from 400 to 500 centipoise at 20 degrees Celsius.

Refractive Index

The refractive index (RI) of a sealing fluid can be, for example, below 1.7, from about 1.4 to about 1.5, from about 1.5 to about 1.6, or about 1.6 to about 1.7.

Contacting

Contacting, for example, a stained specimen with an aqueous sealing fluid, can be by submerging, incubating, applying, soaking, pouring, or layering.

Microscopic Analysis

The term "microscopic analysis" refers to techniques that require a microscope, an instrument or a system that are capable of acquiring data and/or images for analysis. It may be a stand-alone bright-field or fluorescent microscope, a cell imager, a spectrometer, a manual or automated slide stainer and scanner.

The biological specimens can be used in immunological methods, such as immunohistochemistry assays (IHC) and immunocytochemistry assays (ICC). The biological specimens can also be used for in situ hybridization assays (ISH), fluorescent in situ hybridization (FISH) assays, and enzyme-linked immunosorbent assays.

EXAMPLES

The following examples are intended to provide illustrations of the application of the present disclosure. The following examples are not intended to completely define or otherwise limit the scope of the disclosure. One of skill in the art will appreciate that many other methods known in the art may be substituted in lieu of the ones specifically described or referenced herein.

Example 1: Chromogen Protection

A sealing fluid comprising 8% (w/v) Mowiol 4-88 and 10% (w/v) ethanol in water, was used in this example. The sealing fluid was tested with various chromogens to test its effectiveness in preserving stains. The selected chromogens are those frequently used in immunohistochemistry and are known to be at least partially soluble in organic solvents. These organic solvents include those commonly used in mounting media, such as alcohols, xylene, or toluene. Such chromogens are typically used with aqueous mounting medium because they are not compatible with organic-based mounting medium (resinous mounting media). This experiment shows that these chromogens can also be used with organic mounting media (resinous mounting media) when used in combination with the disclosed sealing fluid.

Slides containing tonsil tissue were first stained by immunohistochemistry with an antibody to the Ki67 proliferation marker. This antibody labels lymphocytes undergoing proliferation. After the primary antibody, slides were incubated with a secondary antibody containing either the enzyme horseradish peroxidase or alkaline phosphates. In order to visualize the proliferating cells, the chromogen was applied as the final step in the immunohistochemical sequence. When horseradish peroxidase was used, the chromogen was mixed with the substrate hydrogen peroxide. The reaction of the horseradish peroxidase with the hydrogen peroxide caused the chromogen to precipitate onto the slide leaving a chromogen deposit that was visualized by microscopic examination. When alkaline phosphatase was used, the chromogen was mixed with the substrate naphthol-phosphate. The reaction of alkaline phosphatase with the naphthol-phosphate substrate caused precipitation of the chromogen onto the slide and left a chromogen deposit that was visualized by microscopic examination.

For each chromogen tested two tissue sections were cut from a tissue block. Each tissue section was then applied to one of a pair of microscope slides and prepared for staining. The paired slides were then stained identically, as described above. After the chromogen staining step one slide was left untreated and the other "paired" slide was sealed by incubation with the sealing fluid for five minutes. After incubation, the remaining sealing fluid was drained off of the slides, and the slides were then air-dried. In order to show the effectiveness of the sealing fluid, both the untreated and sealed slides were incubated for three minutes in each of the following reagents: 1) 70% ethanol, 2) 100% ethanol, 3) 50% ethanol/50% xylene, 4) 100% xylene, and 5) 100% xylene. The slides were then mounted with a toluene-based mounting medium (resinous mounting medium) and a glass coverslip was applied.

After mounting, the slides were graded for intensity of stain (chromogen). The intensity of the stain was graded on a scale of 0 to 4, with 0 being no staining, 1 showing faint staining, 2 showing moderate staining, 3 showing strong staining, and 4 showing very strong staining.

As shown in the Table 9 and Table 10, the slides treated with sealing fluid retained strong stain intensity whereas slides not treated with sealing fluid showed partial or complete loss of stain intensity. This example shows the ability of the sealing fluid to protect the stained tissues against the effects of five different solvents.

TABLE 8

Reagents Used in Example 1

| Short Name | Full Name | Vendor | Catalog No. |
|---|---|---|---|
| AEC | Aminoethylcarbazole AEC Staining Kit | Sigma-Aldrich | AEC101-1kT |
| TMB | 3,3',5,5', Tetramethylbenzidine Liquid Substrate System | Sigma-Aldrich | T0565 |
| HRP-Blue | PermaBlue | Diagnostic Biosystems | K063 |
| Fast Red TR | Fast Red TR Salt Kit | Diagnostic Biosystems | K031 |
| New Fuchsin | New Fuchsin Substrate System | Dako Corp. | K069811 |

TABLE 9

Peroxidase

| | Stain Intensity after Mounting | |
|---|---|---|
| Chromogen | With Sealing Fluid | Without Sealing Fluid |
| AEC | 4+ | 0+ |
| TMB | 4+ | 2+ |
| HRP-Blue | 4+ | 1+ |

TABLE 10

Alkaline Phosphatase

| | Stain Intensity after Mounting | |
|---|---|---|
| Chromogen | With Sealing Fluid | Without Sealing Fluid |
| Fast Red TR | 4+ | 0+ |
| New Fuchsin | 4+ | 3+ |

Example 2: Different Polymers

The sealing fluid of Example 1 was tested with different polymers to test the effectiveness of the various polymers in preserving stains. The selected polymers included polyvinyl alcohols (PVAs) and polyvinylpyroliddones (PVPs) of various molecular weights ranging from 27,000 to 200,000. A list of the polymers used along with certain characteristics of each polymer is shown in Table 11. This experiment shows that different polymers can protect chromogens (stains) from being dissolved by organic mounting media (resinous mounting media).

Slides containing tonsil tissue were first stained by immunohistochemistry with an antibody to the Ki67 proliferation marker. This antibody labels lymphocytes undergoing proliferation. After the primary antibody, slides were incubated with a secondary antibody containing either the enzyme horseradish peroxidase or alkaline phosphates. In order to visualize the proliferating cells, the chromogen was applied as the final step in the immunohistochemical sequence. When horseradish peroxidase was used, the chromogen was mixed with the substrate hydrogen peroxide. The reaction of the horseradish peroxidase with the hydrogen peroxide caused the chromogen to precipitate onto the slide leaving a chromogen deposit that was visualized by microscopic examination. When alkaline phosphatase was used, the chromogen was mixed with the substrate naphthol-phosphate. The reaction of alkaline phosphatase with the naphthol-phosphate substrate caused precipitation of the chromogen onto the slide and left a chromogen deposit that was visualized by microscopic examination.

For each polymer tested two tissue sections were cut from a tissue block. Each tissue section was then applied to one of a pair of microscope slides and prepared for staining. The paired slides were then stained identically, as described above. After the chromogen staining step one slide was left untreated and the other "paired" slide was sealed by incubation with the sealing fluid for five minutes. After incubation, the remaining sealing fluid was drained off of the slides, and the slides were then air-dried. In order to show the effectiveness of the sealing fluid, both the untreated and sealed slides were incubated for three minutes in each of the following reagents: 1) 70% ethanol, 2) 100% ethanol, 3) 50% ethanol/50% xylene, 4) 100% xylene, and 5) 100% xylene. The slides were then mounted with a toluene-based mounting medium (resinous mounting medium) and a glass coverslip was applied.

After mounting, the slides were graded for intensity of stain (chromogen). The intensity of the stain was graded on a scale of 0 to 4, with 0 being no staining, 1 showing faint staining, 2 showing moderate staining, 3 showing strong staining, and 4 showing very strong staining.

As shown in Table 12, Table 13, and Table 14, the slides treated with various polymers of PVA and PVP retained strong stain intensity, whereas slides not treated with these polymers showed partial or complete loss of stain intensity.

TABLE 11

Reagents Used in Example 2

| Short Name | Full Name | Molecular Weight | Vendor | Catalog No. |
| --- | --- | --- | --- | --- |
| PVP | Polyvinyl Pyroliddone | 40,000 | Sigma-Aldrich | PVP40 |
| PVA (HM) | Polyvinyl Alcohol High Molecular Weight | 185,000 | Sigma-Aldrich | 363065 |
| PVA (LM) | Polyvinyl Alcohol Low Molecular Weight | 27,000 | Sigma-Aldrich | 81382 |
| Mowiol 40-88 | Polyvinyl Alcohol Mowiol 40-88 | 200,000 | Sigma-Aldrich | 324590 |

TABLE 12

Different Polymers as Sealing Fluid After Staining with TMB

| | Stain Intensity After Mounting | |
| --- | --- | --- |
| Polymer | With Sealing Fluid | Without Sealing Fluid |
| PVP | 4+ | 2+ |
| PVA (LM) | 4+ | 2+ |
| PVA (HM) | 4+ | 2+ |
| Mowiol 40-88 | 4+ | 2+ |

TABLE 13

Different Polymers as Sealing Fluid After Staining with HRP-Blue

| | Stain Intensity After Mounting | |
| --- | --- | --- |
| Polymer | With Sealing Fluid | Without Sealing Fluid |
| PVP | 4+ | 1+ |
| PVA (LM) | 4+ | 1+ |
| PVA (HM) | 4+ | 1+ |
| Mowiol 40-88 | 4+ | 1+ |

TABLE 14

Different Polymers as Sealing Fluid After Staining with Fast Red TR

| | Stain Intensity After Mounting | |
| --- | --- | --- |
| Polymer | With Sealing Fluid | Without Sealing Fluid |
| PVP | 4+ | 0+ |
| PVA (LM) | 4+ | 0+ |
| PVA (HM) | 4+ | 0+ |
| Mowiol 40-88 | 4+ | 0+ |

While certain embodiments have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of sealing a tissue sample to prevent drying artifacts, the method comprising the following steps in the following sequential order:
    a) obtaining the tissue sample;
    b) staining the tissue sample with a stain;
    c) rinsing the tissue sample with an aqueous solution to obtain a hydrated stained tissue sample;
    d) contacting the hydrated stained tissue sample with a sealing fluid, the sealing fluid comprising;
        i) a water-soluble dehydration protectant selected from one of, polyvinyl alcohol and polyvinylpyrrolidone;
        ii) a tissue-penetration agent comprising alcohol for facilitating penetration and infiltration of the water-soluble dehydration protectant into the hydrated stained tissue sample;
    e) drying the hydrated stained tissue sample and the water-soluble dehydration protectant so that the previously hydrated stained tissue sample forms a dehydrated stained tissue sample;

f) forming a thin layer over the dehydrated stained tissue sample as well as infiltrating the dehydrated stained tissue sample with the water-soluble dehydration protectant to prevent drying artifacts; and g) contacting the thin layer formed by the water-soluble dehydration protectant with a mounting media selected from one of a resinous mounting media and an aqueous mounting media, the mounting media contacting the thin layer previously formed by the water-soluble dehydration protectant.

2. The method of claim 1, wherein a) the tissue sample comprises about 25% (w/v) or more water; or b) the stain used to stain the tissue sample is an immunohistochemistry stain, an in-situ hybridization stain, or any stain used in histology; or c) the stain used to stain the tissue sample is soluble in an organic solvent; or d) the stain used to stain the tissue sample is insoluble in an organic solvent; or e) the stain used to stain the tissue sample is: 3-Amino-9-ethylcarbazole (AEC); Fast Red TR; New Fuchsin; 3,3',5,5' Tetramethylbenzidine (TMB); horseradish peroxidase (HRP)-blue; 3,3'-diaminobenzidine; Benzidine; Variamine Blue; Fast Blue BB; Basic Fuchsin; Pararosanaline; an indoxyl phosphate; 6-Chloro-3-indoxyl phosphate 5-Bromo-4-chloro-3-indoxyl phosphate; 3-indoxyl phosphate; a tetrazolium, Nitro blue tetrazolium; Tetranitro blue tetrazolium; or Iodonitro tetrazolium; or f) the stain is a chromogen used in combination with a substrate and an enzyme, wherein the enzyme is a peroxidase, horse radish peroxidase, a phosphatase, or alkaline phosphatase.

3. The method of claim 1, wherein the sealing fluid has a viscosity of about 3 centipoise to about 20 centipoise at 20 degrees Celsius, the viscosity sufficient to both penetrate the tissue sample and form the thin plastic layer over the tissue sample to prevent air drying artifacts.

4. The method of claim 1, wherein the tissue-penetrating agent comprises about 1% (w/v) to about 40% (w/v) of the sealing fluid.

5. The method of claim 1, wherein the sealing fluid further comprises a water-soluble ultraviolet stabilizer at about 0.05% (w/v) to about 15% (w/v).

6. The method of claim 5, wherein the water-soluble ultraviolet stabilizer comprises at least one of; an ultraviolet absorber, an ultraviolent quencher, or a Hindered Amine Light Stabilizer (HALS), 2-phenylbenzimidazole-5-sulfuric acid, a benzophenone, a benzotriazole, a benzoate, rutile titanium oxide, a nickel quencher, a compound with a 2,2,6,6-tramethlypiperidine ring, a 2-hydroxybenzophenone, a 2-hydroxybenzotriazole, a substituted acrylonitrile, or a salicylate.

7. The method of claim 5, wherein the water-soluble ultraviolet stabilizer comprises 2-phenylbenzimidazole-5-sulfuric acid.

8. The method of claim 1, wherein, the sealing fluid has a refractive index (RI) of about 1.4 to about 1.5, of about 1.5 to about 1.6, or about 1.52; or below about 1.7.

* * * * *